(12) United States Patent
McKay

(10) Patent No.: US 9,220,608 B2
(45) Date of Patent: Dec. 29, 2015

(54) FACET JOINT IMPLANT DEVICE

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 68 days.

(21) Appl. No.: 13/454,596

(22) Filed: Apr. 24, 2012

(65) Prior Publication Data
US 2013/0282128 A1 Oct. 24, 2013

(51) Int. Cl.
| A61F 2/30 | (2006.01) |
| A61F 2/28 | (2006.01) |
| A61F 2/44 | (2006.01) |
| A61B 17/70 | (2006.01) |

(52) U.S. Cl.
CPC .......... *A61F 2/4465* (2013.01); *A61B 17/7064* (2013.01); *A61F 2002/2817* (2013.01); *A61F 2002/2835* (2013.01); *A61F 2002/30113* (2013.01); *A61F 2002/30225* (2013.01); *A61F 2002/30448* (2013.01); *A61F 2002/30878* (2013.01); *A61F 2002/30891* (2013.01); *A61F 2310/00179* (2013.01); *A61F 2310/00293* (2013.01); *A61F 2310/00341* (2013.01); *A61F 2310/00359* (2013.01); *A61F 2310/00365* (2013.01)

(58) Field of Classification Search
CPC ...................................... A61F 2/30; A61F 2/28
USPC .............. 606/60, 246–279; 623/17.11–17.16
See application file for complete search history.

(56) References Cited

U.S. PATENT DOCUMENTS

| 5,531,791 | A | 7/1996 | Wolfinbarger et al. |
| 6,652,592 | B1 * | 11/2003 | Grooms et al. ............. 623/23.51 |
| 7,498,041 | B2 | 3/2009 | Masinaei et al. |
| 7,815,682 | B1 | 10/2010 | Peterson et al. |
| 2002/0120338 | A1 | 8/2002 | Boyer, II et al. |
| 2003/0009235 | A1 | 1/2003 | Manrique et al. |
| 2003/0114936 | A1 | 6/2003 | Sherwood et al. |
| 2003/0167092 | A1 | 9/2003 | Foley |
| 2004/0115172 | A1 * | 6/2004 | Bianchi et al. ............... 424/93.7 |
| 2005/0021142 | A1 | 1/2005 | Ganz et al. |
| 2005/0085922 | A1 | 4/2005 | Shappley et al. |
| 2006/0233851 | A1 | 10/2006 | Simon et al. |
| 2006/0280803 | A1 | 12/2006 | Kumar et al. |
| 2006/0293757 | A1 | 12/2006 | McKay et al. |
| 2007/0098756 | A1 | 5/2007 | Behnam |
| 2008/0114465 | A1 | 5/2008 | Zanella et al. |
| 2008/0188945 | A1 * | 8/2008 | Boyce et al. ............... 623/23.61 |
| 2008/0281431 | A1 | 11/2008 | Missos |
| 2009/0130173 | A1 | 5/2009 | Behnam et al. |
| 2009/0155378 | A1 * | 6/2009 | Behnam et al. ............... 424/549 |
| 2009/0192474 | A1 | 7/2009 | Wei et al. |
| 2009/0312842 | A1 * | 12/2009 | Bursac et al. ............. 623/23.72 |
| 2009/0319045 | A1 | 12/2009 | Truncale et al. |
| 2010/0042216 | A1 | 2/2010 | Kilpela et al. |

(Continued)

*Primary Examiner* — Christopher Beccia
(74) *Attorney, Agent, or Firm* — Sorell Lenna & Schmidt LLP

(57) ABSTRACT

A bone graft implant device for treating a tissue site is provided, the device including an implant body including a demineralized allograft bone material portion, and at least one engagement member protruding from the implant body including a mineralized allograft bone material portion. The engagement member may be integrally formed with the implant body, or alternatively, the implant body may include an aperture and the engagement member may be insertable therein. At least one of the amount of demineralization or area of the demineralized allograft bone material portion is adjustable to impart a desired flexibility to the implant body.

20 Claims, 2 Drawing Sheets

(56) References Cited

U.S. PATENT DOCUMENTS

| | | |
|---|---|---|
| 2010/0268232 A1 | 10/2010 | Betz et al. |
| 2010/0286783 A1 | 11/2010 | Lechmann et al. |
| 2011/0144766 A1 | 6/2011 | Kale et al. |
| 2011/0230912 A1* | 9/2011 | Dennis ........................ 606/247 |
| 2013/0017232 A1* | 1/2013 | Varghese et al. .............. 424/400 |

* cited by examiner

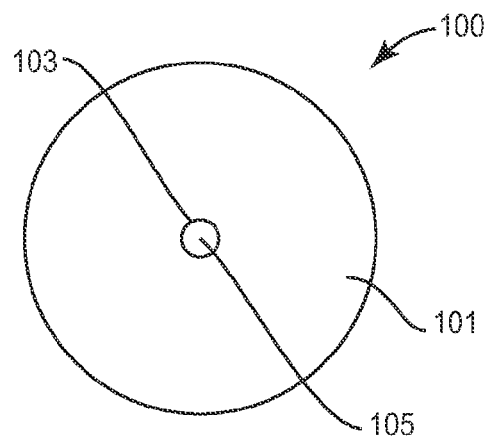
FIG. 1
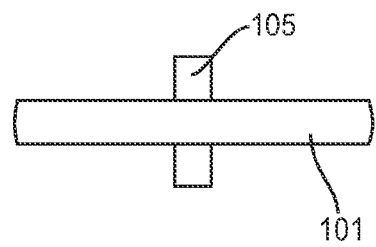
FIG. 2
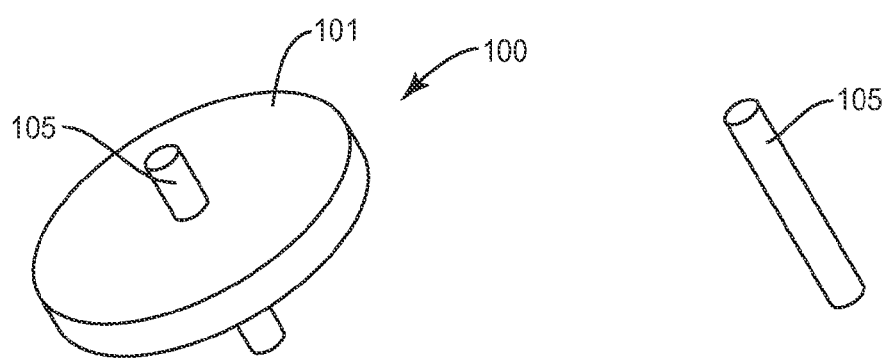
FIG. 3
FIG. 4

FACET JOINT IMPLANT DEVICE

BACKGROUND

The facet joint is a synovial joint between the superior articular process of one vertebra and the inferior articular process of the vertebra directly above it. There are two facet joints in each spinal motion segment. The biomechanical function of each pair of facet joints is to guide and limit movement of the spinal motion segment. In the lumbar spine, for example, the facet joints function to protect the motion segment from anterior shear forces, excessive rotation and flexion. These functions can be disrupted by degeneration, dislocation, fracture, injury, instability from trauma, osteoarthritis, and surgery. In the thoracic spine the facet joints function to restrain the amount of flexion and anterior translation of the corresponding vertebral segment and function to facilitate rotation.

In large part due to the mechanical nature of their function, all joints undergo degenerative changes with the wear and tear of age. This is particularly true for joints in the spine, and the facet joint in particular.

The human spine serves many functions. The vertebral members of the spinal column protect the spinal cord. The spinal column also supports other portions of the human body. Furthermore, moveable facet joints and resilient discs disposed between the vertebral members permit motion between individual vertebral members. Each vertebra includes an anterior body and a posterior arch. The posterior arch includes two pedicles and two laminae that join together to form the spinous process. A transverse process is laterally positioned at the transition from the pedicles to the laminae. Both the spinous process and transverse process provide for attachment of fibrous tissue, including muscle. Two inferior articular processes extend downward from the junction of the laminae and the transverse process. Further, two superior articular processes extend upward from the junction. The articular processes of adjacent vertebrae form the facet joints. The inferior articular process of one vertebra articulates with the superior articular process of the vertebra below. The facet joints are gliding joints because the articular surfaces glide over each other.

Chronic back problems cause pain and disability for a large segment of the population and adverse spinal conditions are characteristic of advancing age. With aging, generally comes an increase in spinal stenosis (including, but not limited to, central canal and lateral stenosis), and facet arthropathy. Spinal stenosis results in a reduction of foraminal area (i.e. the available space for the passage of nerves and blood vessels), which compresses the cervical nerve roots and causes radicular pain. Extension and ipsilateral rotation of the neck further reduces the foraminal area and contributes to pain, nerve root compression, and neural injury.

Neck and arm pain is a common ailment of the aging spine due to disc herniations, facet arthropathy and thickening of spinal ligaments which narrow spinal canal dimensions. This results in compression of the spinal cord or nerve roots, or both. Radicular pain is typically due to disc herniation and foraminal narrowing, which compresses the cervical nerve roots and causes radicular pain. Extension and ipsilateral rotation of the neck further reduces the foraminal area and contributes to pain, nerve root compression, and neural injury. Neck flexion generally increases the foraminal area.

Cervical disc herniations predominantly present upper extremity radicular symptoms. The vast majority of these herniations do not have an associated neurological deficit and present pain only. A well-described treatment for cervical disc herniations is closed traction. There are a number of marketed devices that alleviate pain by pulling on the head to increase foraminal height.

Cervical disc herniations have been treated with anterior and posterior surgery. The vast majority of these surgeries are performed through an anterior approach, which requires a spinal fusion. These surgeries are expensive and beget additional surgeries due to change in biomechanics of the neck. There is a three percent incidence of re-operation after cervical spine surgery.

Vertebral implants are often used in the surgical treatment of spinal disorders such as degenerative disc disease, disc herniations, curvature abnormalities, and trauma. Many different types of treatments are used. Spine fusion surgery is migrating to a more mid-line minimal access approach. Solid fusion in the facets can help to stabilize a motion segment and potentially augment instrumentation. In some cases, spinal fusion is indicated to inhibit relative motion between vertebral bodies. Spinal fusion often involves the removal of the vertebral disc and insertion of an interbody implant to create a fused junction between a pair of vertebral bodies. Furthermore, the facet joints may be fused to complete the fusion between vertebral pairs. Facet fusion often involves destruction of the facet by decorticating the opposing articulating surfaces and packing bone growth promoting substances such as grafts or synthetic materials into the space between the articular processes.

The facet joints are generally small as compared to the intervertebral space. Consequently, limited amounts of bone-growth promoting substances may be inserted into the joint. Some of the bone-growth promoting substances tend to disperse post-operatively resulting in a less robust fusion. Furthermore, the overlying fibrous tissue may further disperse the bone-growth promoting substances as a result of contact, friction, and/or the ingrowth of fibrous mass. These and other factors may result in pseudarthrosis or inadequate fusion.

The use of bone grafts and bone substitute materials in orthopedic medicine is known. While bone wounds can regenerate without the formation of scar tissue, fractures and other orthopedic injuries take a long time to heal, during which time the bone is unable to support physiologic loading unaided. Metal pins, screws, rods, plates and meshes are frequently required to replace the mechanical functions of injured bone. However, metal is significantly more stiff than bone. Use of metal implants may result in decreased bone density around the implant site due to stress shielding. Physiologic stresses and corrosion may cause metal implants to fracture. Unlike bone, which can heal small damage cracks through remodeling to prevent more extensive damage and failure, damaged metal implants can only be replaced or removed. The natural cellular healing and remodeling mechanisms of the body coordinate removal of bone and bone grafts by osteoclast cells and formation of bone by osteoblast cells.

Conventionally, bone tissue regeneration is achieved by filling a bone repair site with a bone graft. Over time, the bone graft is incorporated by the host and new bone remodels the bone graft. In order to place the bone graft, it is common to use a monolithic bone graft or to form an osteoimplant comprising particulated bone in a carrier. The carrier is thus chosen to be biocompatible, to be resorbable, and to have release characteristics such that the bone graft is accessible. Generally, the formed implant, whether monolithic or particulated and in a carrier, is substantially solid at the time of implantation and thus does not conform to the implant site. The use of bone grafts is generally limited by the available shape and size of grafts. Bone grafts using cortical bone remodel slowly because of their limited porosity. Traditional bone substitute materials and bone chips are more quickly remodeled but cannot immediately provide mechanical support. In addition, while bone substitute materials and bone chips can be used to fill oddly shaped bone defects, such materials are not as well suited for wrapping or resurfacing bone.

Demineralized bone matrix (DBM) is a manufactured product that has been readily available for over ten years. DBM is demineralized allograft bone with osteoinductive activity. DBM is prepared by acid extraction of allograft bone, resulting in loss of most of the mineralized component but retention of collagen and noncollagenous proteins, including growth factors. DBM does not contain osteoprogenitor cells, but the efficacy of a demineralized bone matrix as a bone-graft substitute or extender may be influenced by a number of factors, including the sterilization process, the carrier, the total amount of bone morphogenetic protein (BMP) present, and the ratios of the different BMPs present. DBM includes demineralized pieces of cortical bone to expose the osteoinductive proteins contained in the matrix. These activated demineralized bone particles are usually added to a substrate or carrier (e.g. glycerol or a polymer). DBM is mostly an osteoinductive product, but lacks enough induction to be used on its own in challenging healing environments such as posterolateral spine fusion.

Allograft bone is a reasonable graft substitute for autologous bone. It is readily available from cadavers and avoids the surgical complications and patient morbidity associated with harvesting autologous bone. Allograft bone is essentially a load-bearing matrix comprised of cross-linked collagen, hydroxyapatite, and osteoinductive Bone Morphogenetic Proteins (BMP). Human allograft tissue is widely used in orthopedic surgery.

Even though allograft has certain advantages over the other treatments, one of the main drawbacks of the allograft treatment is that the ingrowth of the host bone into the grafted bone may take longer than in an autograft. As a result, allograft treatment may be less effective than the autograft. Despite the advances recently made in the art, new methods promoting ingrowth of the host bone into the grafted bone are needed to better utilize the advantages of allograft treatment.

Current concepts of using allograft implants in a facet fusion involve mineralized pieces of allograft that are threaded across the joint or impacted into place. These cortical allograft implants can take a very long time to attach and incorporate with the host bone ultimately resulting in a fusion. These solid implants also require specialized preparation of the facet joint for the cortical bone implants to fit into place. Many times these preparation instruments require removal of a significant amount of the facet joint leading to further destabilization.

Thus, there is a need for minimally invasive methods and devices for improving and accelerating fusion of an implant with the facet joint, therefore ultimately reducing radicular symptoms for patients with soft and hard disc disease.

SUMMARY

Implant devices insertable into a graft site, namely, a vertebral facet joint, and methods of using same are provided. In some embodiments, implant bodies comprising mineralized and demineralized portions are provided for delivery to a facet joint.

In one embodiment, a bone graft implant device for treating a tissue site is provided, the device comprising an implant body including a demineralized portion; and at least one engagement member protruding from the implant body comprising a mineralized portion.

In another embodiment, a bone graft implant device for treating a facet joint is provided, the device comprising an implant body comprising demineralized allograft bone material; and at least one engagement member protruding from the implant body comprising mineralized allograft bone material.

In yet another embodiment, a bone graft implant device for treating a facet joint is provided, the device comprising an implant body comprising a demineralized allograft bone material portion; and at least one engagement member formed to be integral with and protrude from the implant body, said at least one engagement member comprising mineralized allograft bone material.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 1 illustrates a top view of an exemplary implant device according to an aspect of the present application;

FIG. 2 illustrates a side view of the exemplary implant device of FIG. 1 according to an aspect of the present application;

FIG. 3 illustrates a perspective view of the exemplary implant device of FIG. 1 according to an aspect of the present application; and FIG. 4 illustrates an exemplary facet joint engagement member according to an aspect of the present application.

Figure 5:
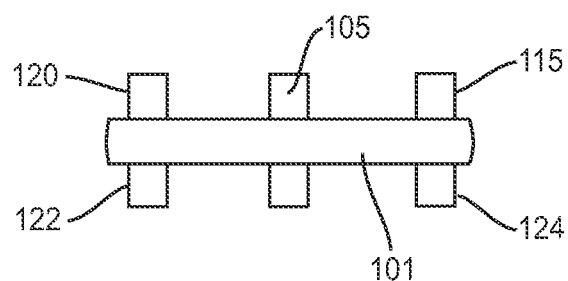
FIG. 5 illustrates another exemplary facet joint engagement member according to an aspect of the present application.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

"Bioactive Agent or Bioactive Compound," as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD.

"Biocompatible," as used herein, refers to materials that, upon administration in vivo, do not induce undesirable long-term effects.

"Bone," as used herein, refers to bone that is cortical, cancellous or cortico-cancellous of autogenous, allogenic, xenogenic, or transgenic origin.

"Demineralized," as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the disclosure. In some embodiments, demineralized bone has less than 95% of its original mineral content. Demineralized is intended to encompass such expressions as "substantially demineralized," "partially demineralized," and "fully demineralized." In some embodiments, part or all of the surface of the bone can be demineralized. For example, part or all of the surface of the allograft can be demineralized to a depth of from about 100 to about 5000 microns, or about 150 microns to about 1000 microns. If desired, the outer surface of the intervertebral implant can be masked with an acid resistant coating or otherwise treated a to selectively demineralize unmasked portions of the outer surface of the intervertebral implant so that the surface demineralization is at discrete positions on the implant.

"Demineralized bone matrix," as used herein, refers to any material generated by removing mineral material from bone tissue. In some embodiments, the DBM compositions as used herein include preparations containing less than 5% calcium and preferably less than 1% calcium by weight. Partially demineralized bone (e.g., preparations with greater than 5% calcium by weight but containing less than 100% of the original starting amount of calcium) are also considered within the scope of the disclosure.

"Osteoconductive," as used herein, refers to the ability of a non-osteoinductive substance to serve as a suitable template or substance along which bone may grow.

"Osteogenic," as used herein, refers to the ability of an agent, material, or implant to enhance or accelerate the growth of new bone tissue by one or more mechanisms such as osteogenesis, osteoconduction, and/or osteoinduction.

"Osteoimplant," as used herein, refers to any bone-derived implant prepared in accordance with the embodiments of this disclosure and therefore is intended to include expressions such as bone membrane, bone graft, etc.

"Osteoinductive," as used herein, refers to the quality of being able to recruit cells from the host that have the potential to stimulate new bone formation. Any material that can induce the formation of ectopic bone in the soft tissue of an animal is considered osteoinductive.

"Superficially demineralized," as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "morbidity" refers to the frequency of the appearance of complications following a surgical procedure or other treatment.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

The term "osteogenic" refers to the ability of a graft material to produce bone independently. To have direct osteogenic activity, the graft must contain cellular components that directly induce bone formation. For example, a collagen matrix seeded with activated MSCs would have the potential to induce bone formation directly, without recruitment and activation of host MSC populations. Because many osteoconductive scaffolds also have the ability to bind and deliver bioactive molecules, their osteoinductive potential will be greatly enhanced.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

The term "xenograft" refers to tissue or organs from an individual of one species transplanted into or grafted onto an organism of another species, genus, or family.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a facet engaging feature" includes one, two, three or more features.

Reference will now be made in detail to certain embodiments of the application, examples of which are illustrated in the accompanying drawings. While the application will be described in conjunction with the illustrated embodiments, it will be understood that they are not intended to limit the application to those embodiments. On the contrary, the application is intended to cover all alternatives, modifications, and equivalents, which may be included within the application as defined by the appended claims.

The headings below are not meant to limit the disclosure in any way; embodiments under any one heading may be used in conjunction with embodiments under any other heading.

Each spinal column vertebrae has two facet joints, with facet joints between adjacent facets of the vertebrae. The spinal cord passes vertically through the aligned vertebrae with peripheral nerves passing from the spinal cord outwardly through the spinal column through foraminal openings to predestined locations in the human body. When facet joints become narrowed, usually from disc degeneration, the foraminal openings are reduced in size pinching the nerve and causing pain to the individual.

Implant devices and methods of using same are provided in the present application for insertion into an intra-facet space to facilitate fusion of the facet joint. In various embodiments, a cortical allograft implant body having mineralized and demineralized portions is provided. According to some embodiments, a demineralized allograft implant body comprising a disc-shape is provided having at least one mineralized facet engagement feature which is formed to be integral with one or more sides of the body, or inserted within an aperture formed in the body.

Advantageously, an implant device according to the present application comprises a combination of materials having different attributes and in specific configurations so as to be structurally flexible to facilitate delivery of the device into facet joint spaces, while providing improved retention and fusion of the device within the facet joint.

In some embodiments, an implant device according to the present application is specifically designed to fuse a tissue site such as a facet joint. In some embodiments, an implant device comprises a partially demineralized allograft disc that has some inherent structural flexibility and mineralized portions. Advantageously, the flexibility imparted by the demineralized areas allows for the allograft disc to be inserted into complex three dimensional curved facet joint shapes, as well as facilitates faster fusion by exposing the inherent bone morphogenetic proteins (BMP) factors in cortical allograft. The mineralized areas allow for mechanical distraction of the facet joint so fusion occurs in a more anatomically correct position. In some embodiments, the mineralized areas comprise mineralized protrusions in the center of one or both sides of the disc that engage with the face of each facet to retain the disc in place.

Advantageously, an implant device according to the present application facilitates effective fusion while only necessitating removal of soft tissues from the facet joint and is easy to insert into the tissue site. Even though the facet has a somewhat complicated surface geometry, the flexible implant body allows for easy insertion due to its partial flexibility. According to yet another advantageous feature, at least one of the amount of demineralization and/or the areas or portions of the disc that are demineralized can be adjusted to impart the desired amount of flexibility to the implant body. The demineralized portion facilitates new bone formation relatively quickly compared to a solid cortical disc, thus accelerating the facet fusion process.

In some embodiments, the surface demineralized region will have a modulus of elasticity in the range of about $1 \times 10^2$ to about $3 \times 10^6$ dynes/cm$^2$, or $1 \times 10^5$ to about $2 \times 10^5$ dynes/cm$^2$, or $5 \times 10^4$ to about $1 \times 10^6$ dynes/cm$^2$.

Various designs and configurations of the partially/selectively demineralized allograft implant are contemplated. The location and amount of the demineralized and mineralized areas of the disc may be strategically and selectively provided in a number of ways to optimize the insertion and incorporation process. While a disc-shape body is shown in FIGS. 1-3, alternate implant body shapes may be contemplated.

The implant devices according to the present application may be handled, inserted and delivered using various surgical implant delivery devices, preferably following preparation and distraction of a tissue site.

In some embodiments, implant devices according to the present application may be delivered using surgical devices via an access system such as an access port (e.g., a minimal access port), for example, dilators which may progressively increase in diameter size. For example, dilators may be inserted sequentially (smaller to larger) through a tissue site to gradually separate, or split, and open the tissue to create an opening large enough for the surgical devices to be used. The dilator tubes may be used to maintain the opening while surgical devices to reach the site are inserted within the tubes. A kit comprising a graft preparation instrument, a distraction device, a graft delivery device and an implant body may be provided.

Referring to the Figures, FIGS. 1-3 depict top, side and perspective views of an exemplary implant device according to aspects of the present application. FIG. 4 depicts an exemplary facet engagement member according to an aspect of the present application.

Pursuant to one aspect of the present application, an implant device 100 is provided comprising a disc-shaped body 101 having an aperture 103 formed therein. The aperture 103 may be formed part way through or pass entirely through the body 101. While a disc-shape is shown, the bone graft body 101 may be machined into any shape or configuration and to include features such as grooves, protrusions, indentations, etc., to help improve fit and limit any movement or micromotion of the allograft block to help fusion to occur. In some embodiments, the aperture 103 is provided in substantially a center of the body 101, and may comprise a circular shape as shown. Alternate locations, configurations and dimensions of the aperture 103 may be contemplated.

In some embodiments, the surface of the implant device can be, for example, rough, arcuate, undulating, crescent, dimpled, polished and/or textured according to the requirements of a particular application. It is contemplated that implant may be oval, oblong, triangular, rectangular, square, polygonal, irregular, tubular, non-tubular, uniform, non-uniform, variable and/or tapered.

In some embodiments, there may be a plurality of apertures in the implant that allow cells and material through the implant and to the target tissue site to enhance bone growth. In some embodiments, the implant comprises a plurality of apertures. In some embodiments, at least 10% of the apertures are between about 10 micrometers and about 500 micrometers at their widest points. In some embodiments, at least 20% of the apertures are between about 50 micrometers and about 150 micrometers at their widest points. In some embodiments, at least 30% of the apertures are between about 30 micrometers and about 70 micrometers at their widest points. In some embodiments, at least 50% of the apertures are between about 10 micrometers and about 500 micrometers at their widest points. In some embodiments, at least 90% of the apertures are between about 50 micrometers and about 150 micrometers at their widest points. In some embodiments, at least 95% of the apertures are between about 100 micrometers and about 250 micrometers at their widest points. In some embodiments, 100% of the apertures are between about 10 micrometers and about 300 micrometers at their widest points.

In some embodiments, the apertures in the implant can be as large as 2000 microns to allow cells through. In some embodiments, the apertures of the implant can be in the range of from about 500 microns to about 1500 microns.

According to some embodiments, the body 101 may comprise a cortical allograft material which is at least partially or entirely demineralized. That is, the body 101 may include demineralized portions or entirely comprise demineralized allograft material. At least one of the amount of demineralization of the demineralized portions and/or the areas of the demineralized portions may be adjustable to provide an implant body 101 having the desired amount of flexion and deformability. The demineralized allograft may comprise, e.g., surface demineralized allograft.

In some embodiments, part or all of the surface of the implant can be demineralized. For example, part or all of the surface of the allograft can be demineralized to a depth of from about 50 to about 5000 microns, or about 100 microns to about 1000 microns. If desired, the outer surface of the intervertebral implant can be masked with an acid resistant coating or otherwise treated a to selectively demineralize unmasked portions of the outer surface of the intervertebral implant so that the surface demineralization is at discrete positions on the implant.

In some embodiments, the implant is configured to increase the surface area contact of the allograft with the host bone, which will result in faster fusion and incorporation of the implant into host bone and ultimately a stronger fusion mass. In some embodiments, the implant optimizes location such that the majority of the mechanical load is carried by the portion of the allograft that is not demineralized. Therefore, the load bearing characteristics and/or higher compressive strength will be directed to the allograft material comprising cortical bone, while areas that will be subjected to less load bearing and less compressive strenght will comprise demineralized bone material.

In some embodiments, the implant device contacts host bone and the implant device comprises non-bone material, the contact surface area of the non-bone material and the cortical bone to the host bone comprises from about 5% to about 50% or from about 10% to about 20% of the implant.

In some embodiments, the implant device contacts host bone and the implant device comprises 5% to about 50% by weight of demineralized bone matrix material based on the total weight of the implant, while 95% to about 50% by weight of the implant comprises non-demineralized bone material.

In some embodiments, the implant device comprises non-bone material and the non-bone material comprises from about 10 wt. % to about 60 wt. % of the implant. In some embodiments, the implant device comprises bone material and the bone material comprises from about 10 wt. % to about 60 wt. % of the implant.

In some embodiments, the implant device comprises non-bone material and the non-bone material comprises from about 10 wt. % to about 60 wt. % of the implant. In some embodiments, the implant device comprises bone material and the bone material comprises from about 10 wt. % to about 60 wt. % of the implant.

Advantageously, the demineralized bone graft body imparts improved osteoconductivity and osteoinductivity for facilitating bone fusion, for example, interspinous process fusion, and also provides structural flexibility, thus allowing the body 101 to be insertable into complex joint regions, such as curved facet joint spaces.

In some embodiments the demineralized allograft bone material may include, be imparted with, or comprise an additive such as an angiogenesis promoting material or a bioactive agent. It will be appreciated that the amount of additive used may vary depending upon the type of additive, the specific activity of the particular additive preparation employed, and the intended use of the composition. The desired amount is readily determinable by one skilled in the art. Angiogenesis may be an important contributing factor for the replacement of new bone and cartilage tissues. In certain embodiments, angiogenesis is promoted so that blood vessels are formed at an implant site to allow efficient transport of oxygen and other nutrients and growth factors to the developing bone or cartilage tissue. Thus, angiogenesis promoting factors may be added to the substance to increase angiogenesis. For example, class 3 semaphorins, e.g., SEMA3, controls vascular morphogenesis by inhibiting integrin function in the vascular system, and may be included in the recovered hydroxyapatite.

In accordance with some embodiments, the demineralized allograft bone material may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; demineralized bone powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other means; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immunosuppressants; permeation enhancers, e.g., fatty acid esters such as laureate, myristate and stearate monoesters of polyethylene glycol, enamine derivatives, alpha-keto aldehydes, etc.; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

In some embodiments, an ionic force change agent may be applied to further modify the demineralized or mineralized portions of the allograft bone material. That is, in some embodiments, the disclosure involves the addition of an ionic force change agent to the demineralized and/or demineralized portions of the allograft bone material thereby modifying its surface, namely modifying its charge in a targeted manner to produce an appropriately charged demineralized allograft bone material. The ionic force change agent may be applied to the entire allograft bone material or to selected portions/surfaces thereof.

According to some embodiments, the ionic force change agent may be a binding agent, which modifies the demineralized bone material or bone graft structure to bind molecules, such as, for example, growth factors, or cells, such as, for example, cultured cells, or a combination of molecules and cells. In the practice of the disclosure the growth factors include but are not limited to BMP-2, rhBMP-2, BMP-4, rhBMP-4, BMP-6, rhBMP-6, BMP-7[OP-1], rhBMP-7, GDF-5, LIM mineralization protein, platelet derived growth factor (PDGF), transforming growth factor-beta (TGF-beta), insulin-related growth factor-I (IGF-I), insulin-related growth factor-II (IGF-II), fibroblast growth factor (FGF), beta-2-microglobulin (BDGF II), and rhGDF-5. A person of ordinary skill in the art will appreciate that the disclosure is not limited to growth factors only. Other molecules can also be employed in the disclosure. For example, tartrate-resistant acid phosphatase, which is not a growth factor, may also be used in the disclosure.

If a cell culture is employed, the cells include but are not limited to mesenchymal stems cells, pluripotent stem cells, embryonic stem cells, osteoprogenitor cells, osteoblasts, osteoclasts, and any bone marrow-derived cell lines.

In one embodiment of the method of the disclosure, the ionic forces of the demineralized bone material are changed by a one-to-one substitution of the calcium ion with an element selected from the group consisting of lithium, sodium, potassium and cesium ions of hydroxyapatite.

In some embodiments, the body 101 may include an engagement member 105 comprising one or more protrusions. The engagement member 105 may comprise protrusions formed to be integral with the body 101 (e.g., the engagement member 105 may be machined as one piece with the body 101) and/or may comprise an elongate pin-shaped member insertable within the aperture 103 of the body 101. The engagement member 105 may be formed to protrude from one or more surfaces/sides of the body 101. For example, the engagement members 105 may be configured to protrude from opposing sides of the body 101, as shown, e.g., in FIGS. 2 and 3. In various embodiments, the engagement member 105 comprises allograft bone material, which includes demineralized portions or is entirely mineralized.

In one embodiment, an engagement member 105 may be provided configured to be insertable into the aperture 103 formed in the body 101. The engagement member 105 may comprise an elongate pin-shaped member comprising mineralized portions of allograft bone material, or entirely comprises mineralized allograft bone material.

Advantageously, the combination of demineralized portion of the body 101 with a mineralized engagement member(s) provide increased ease of insertion with minimal damage to the facet joint, while providing improved and accelerated fusion of the device with the facet joint. Namely, the incorporation of mineralized engagement member 105 with one or more sides of the body 101 help to limit motion and keep the implant device 100 in place during the fusion process. The mineralized engagement member(s) 105 helps reduce excessive motion in the facet joint, which facilitates fusion to occur and at a faster rate.

The device 100 having engagement members 105 may be implanted by articulating the spine to open the facet, inserting and press-fitting the implant device 100 into the intra-facet space, and allowing the spine to return to its normal position. Corresponding holes, grooves, indentations or apertures may be made in the surface of the facet joint faces for securing the engagement members 105, further preventing the implant device 100 from sliding out of position or moving after implantation. Most spinal fusions also involve an interbody and/or a posterolateral fusion with instrumentation fixation which will limit motion and keep the facet discs in place during the fusion process.

While an exemplary implant body 101 has been depicted in the shape of a flattened cylinder/disc herein, permanent implants can vary in geometry, material, and fixation mechanism. For example with respect to geometry, a wedge shaped implant can provide for a greater height of the posterior aspect of the implant relative to the anterior aspect of the implant. The wedge can also provide for uniform dimensions at the lateral and medial aspects of the implant. The wedge shape may result in a translating vector force and a separating vector force that results in both subluxation and distraction, thereby increasing the foraminal space more fully. A double wedged implant can provide greater height of the posterior aspect of the implant relative to the anterior aspect of the implant in addition to greater height of the lateral aspect of the implant relative to the medial aspect of the implant. Other geometrical variations can include a flat rectangular shape, an oval pill shape, a concave superior surface, a concave inferior surface, a convex superior surface, a convex inferior surface, a convex anterior surface, a concave anterior surface, a convex posterior surface, and a concave posterior surface.

In some embodiments, the implant device can have a plurality (e.g., two, there, four, five, six, etc.) protrusions on each side of the allograft disc to prevent rotation of the allograft disc when it is implanted into the facet joint. In this way, the protrusions can correspond to corresponding recesses in the bone or facet joint and the protrusions can mate with the corresponding recesses in the bone. These recesses in the bone can be drilled before the device is implanted and are configured to mate with the protrusions of the implant device.

In some embodiments, the implant device can be implanted in various ways, for example, if the two protrusions are integral to the disc, the surgeon could use a drill guide to drill two holes across the facet joint with a drill template and then snap the allograft disc in place by distracting the facet joint open. In other embodiments, the two or more protrusions can not be integral to the surface of the disc, the surgeon can place the allograft disc in the facet joint with and insertion instrument and hold it in place while the surgeon drills two holes across the facet joint and through the allograft disc then insert the two mineralized pins across the facet joint holding the allograft disc in place and further limiting facet micromotion of the disc.

Referring to FIG. 5, it illustrates another embodiment of the implant device. The implant device comprises a disc-shaped body 101 and engagement members 105, 115, 120, on one of its surfaces and on the opposed surface engagement members 122 and 124 these are shown as protrusions or pins extending from the body. These projections or pins extend from the body and can be one continuous projection or pin that extends through the body, and the aperture (103 in FIG. 1) is configured to receive the projection or pin so that the projection or pin extends from the body in its upper and lower surfaces. In this way corresponding recesses can be drilled into bone (e.g., facet joint) and the disc shaped body 101 and corresponding projections or pin can be inserted into the drilled recesses. Accordingly, micromotion of the device after it is implanted is limited. In some embodiments, the disc-shaped body can comprise apertures in it and the bones can have corresponding holes drilled in it and the disc shaped body holes can be aligned with the drilled holes in the bones and the projections or pins can be inserted through the holes of the implant body and the holes of the bone to hold the implant device in position. In some embodiments, the holes of the disc-shaped body and the holes of the bone can be the same or smaller diameter than the diameter of the projections or pins. In this way upon exertion of pressure, the projections or pin will fit snug in the hole or friction fit in the hole to secure the implant device in position. In some embodiments, an adhesive or glue can be used to keep the projections or pins in position.

In some embodiments, the disc-shaped body has portions that are optionally surface demineralized, while the protrusions or pins are fully mineralized cortical bone.

Figure 6:
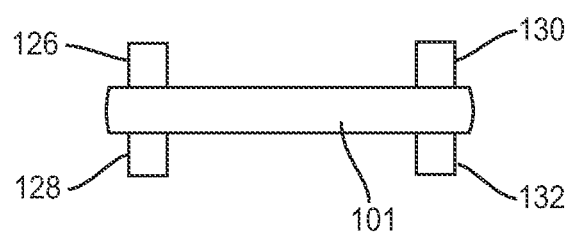
FIG. 6 illustrates yet another exemplary facet joint engagement member according to an aspect of the present application.

Referring to FIG. 6, it illustrates another embodiment of the implant device. The implant device comprises a disc-shaped body 101 and engagement members 126, 130 on one of its surfaces and on the opposed surface engagement members 128, 132 these are shown as protrusions or pins extending from the body. These projections or pins extend from the body and can be one continuous projection or pin that extends through the body, and the aperture (103 in FIG. 1) is configured to receive the projection or pin so that the projection or pin extends from the body in its upper and lower surfaces. In this way corresponding recesses can be drilled into bone (e.g., facet joint) and the disc shaped body 101 and corresponding projections or pin can be inserted into the drilled recesses. Note there is no center pin in this embodiment. Although the projections or pins are shown as the same size, in some embodiments, they can be the same or different shapes and sizes. For example, the projections or pins can be rough, arcuate, undulating, crescent, dimpled, polished and/or textured according to the requirements of a particular application. It is contemplated that the projections or pins may be oval, oblong, triangular, rectangular, square, polygonal, irregular, tubular, non-tubular, uniform, non-uniform, variable and/or tapered. These can match the recesses of the holes in the bone so that the implant can fit within the recesses and stay in position.

In some embodiments, the device can have a plurality of projections or pins disposed at discrete portions to further anchor the device.

In some embodiments, the device can have a diameter of from about 5 mm to about 20 mm to cover both cervical and lumbar uses. In some embodiments, the device can have a diameter of from about 10 mm to about 15 mm to use for the lumbar facets. The thickness of the device can be in the range of about 2 mm to about 10 mm to cover cervical and lumbar uses. In some embodiments, the thickness of the device can be from about 5 mm to about 8 mm for use in the lumbar facets. In some embodiments, the projection or pin can have a diameter of from about 2 mm to about 5 mm. In some embodiments, the projection or pin can have a diameter of from about 3 mm to about 4 mm for use in the lumbar facets. They will stick out from the disc by about 2 mm to about 10 mm or by about 3 mm to about 6 mm when used in the lumbar facets.

The allograft material for the implant may comprise additional material to aid in implantation or retaining the implant at the tissue site. In some embodiments, this additional material may comprise inorganic material, such as an inorganic ceramic and/or bone substitute material. Exemplary inorganic materials or bone substitute materials include but are not limited to aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™, fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

With respect to materials, the graft material may include various additional fixation mechanisms or friction structures, such as a plurality of threads, protrusions, ridges and the like. The additional fixation mechanisms/structures may include mineralized portions or be entirely demineralized. For example, aggressive shark teeth can be provided with a directional orientation positioned to achieve optimal fixation relative to the natural biomechanics of various sections of the spine. The teeth can be long enough to gain purchase in the cortical bone of the facet surfaces. Cleats can also be provided that have a less aggressive profile than the shark teeth but still allow for directional orientation for the same reasons described above. These cleats can also be capable of anchoring in the hard cortical bone of the facet surface. Additionally, a roughened pore surface can be provided to prevent free sliding of the implant within the facet joint. These surfaces can be roughened and coated with commercially available resurface chemicals that would create friction and prevent device migration.

Any or all of the implants devices according to the present application can be adapted as fusion type implants or motion preservation type devices. Implants with varying degrees of motion preservation can also be provided. In the case of a motion preservation type implant, the implant can have fixation mechanisms on one side to enable both temporary and permanent fixation to one surface of the facet joint while allowing the opposing facet surface to slide freely across the surface of the implant. The facet joint can be a naturally sliding joint and a distraction implant with fixation on only one side may accommodate the natural sliding of the facet. However, in some circumstances, a fusion type implant can be more suitable. In these circumstances the implant can include fixation mechanisms on both sides of the implant.

In some embodiments, the implant can be freeze dried so as to preserve growth factors, osteoinductivity and shelf life of the device.

Sterilization

The implant device as well as any site preparation device, distraction device and/or delivery device used therewith may be lightweight, disposable and sterilizable. In various embodiments, one or more components of each device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of each device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize one or more components of each device, including, but not limited to, gas sterilization, such as, for example, with ethylene oxide or steam sterilization.

In various embodiments, a kit is provided for preparing and delivering an implant to a tissue site, the kit comprising one or more of the following: a sterilized graft preparation device, a sterilized distraction device, a sterilized implant delivery device and an implant device.

In various embodiments, a kit is provided which may include additional parts along with the preparation, distraction and/or delivery devices and implant device. The kit may include the preparation, distraction and delivery devices in a first compartment. The second compartment may include implant devices of varying configurations, shapes and sizes. A third compartment may include an access system, and any other instruments needed for the implant. A fourth compartment may include gloves, drapes, wound dressings and other procedural supplies for maintaining sterility of the implanting process, as well as an instruction booklet. Each tool and component may be separately packaged in a plastic pouch that is radiation sterilized. A cover of the kit may include illustrations of the implanting procedure and a clear plastic cover may be placed over the compartments to maintain sterility.

Although the present invention has been described with a certain degree of particularity, it is understood the disclosure has been made by way of example, and changes in detail or structure may be made without departing from the spirit of the invention as defined in the appended claims. It is to be understood that the features of any given embodiment can be combined with features of other embodiments and still be within the scope of the invention. Where functionality allows, interchanging certain features of one embodiment with another embodiment is within the scope of the present invention. Thus, it is intended that various embodiments cover other modifications and variations of various embodiments within the scope of the present teachings.

What is claimed is:

1. A bone graft implant device for treating a tissue site, the device comprising:
   an implant body including a demineralized portion, the implant body having an outer surface comprising fully demineralized portions and surface demineralized portions located at discrete positions on the outer surface of the implant, the discrete positions being surface demineralized to a depth of about 50 microns to about 5000 microns, the implant body comprising a modulus of elasticity in the range of about $1 \times 10^5$ to about $2 \times 10^5$ dynes/cm$^2$; and
   at least one engagement member protruding from the demineralized portion, the engagement member comprising only a mineralized portion.

2. A bone graft implant device of claim 1, wherein the implant body comprises a disc shape.

3. A bone graft implant device of claim 1, wherein the implant body comprises allograft bone material.

4. A bone graft implant device of claim 1, wherein the demineralized portion comprises demineralized allograft bone material.

5. A bone graft implant device of claim 1, wherein the mineralized portion of the engagement member comprises mineralized allograft bone material.

6. A bone graft implant device of claim 5, wherein the engagement member is integrally formed with the implant body and comprises at least one protrusion formed on at least one surface of the implant body.

7. A bone graft implant device of claim 5, wherein the implant body further includes an aperture extending into the demineralized portion.

8. A bone graft implant device of claim 7, wherein (i) the engagement member comprises an elongate pin-shaped member configured to be insertable within said aperture or (ii) the engagement member comprises an elongate pin-shaped member configured to be mate with a corresponding recess in bone.

9. A bone graft implant device of claim 1, wherein the tissue site comprises an intra-facet joint space.

10. A bone graft implant device of claim 1, wherein at least one of the amount of demineralization or area of the demineralized portion is adjustable to impart a desired flexibility to the implant body.

11. A bone graft implant device for treating a facet joint, the device comprising:
   an implant body comprising demineralized allograft bone material defining a demineralized portion, the implant body having an outer surface comprising an acid resistant coating configured to mask portions of the outer surface and to allow unmasked portions of the outer surface to be surface demineralized such that surface demineralization is at discrete positions on the implant, the discrete positions being surface demineralized to a depth of about 50 microns to about 5000 microns; and
   at least one engagement member protruding from the demineralized portion, the engagement member comprising only mineralized allograft bone material.

12. A bone graft implant device of claim 11, wherein the implant body comprises a disc shape.

13. A bone graft implant device of claim 11, wherein the engagement member is integrally formed with the implant body and comprises at least one protrusion formed on at least one surface of the implant body.

14. A bone graft implant device of claim 11, wherein the implant body further includes an aperture extending through the demineralized portion.

15. A bone graft implant device of claim 14, wherein the engagement member comprises an elongate pin-shaped member configured to be insertable within said aperture.

16. A bone graft implant device of claim 11, wherein the amount of demineralization of the demineralized portion is adjustable to impart a desired flexibility to the implant body.

17. A bone graft implant device for treating a facet joint, the device comprising:
   an implant body comprising a demineralized allograft bone material portion, the implant body having an outer surface comprising an acid resistant coating configured to mask portions of the outer surface and to allow unmasked portions of the outer surface to be surface demineralized such that surface demineralization is at discrete positions on the implant, the discrete positions being surface demineralized to a depth of about 50 microns to about 5000 microns; and
   at least one engagement member formed to be integral with and protrude from the demineralized allograft bone material portion, said at least one engagement member comprising only mineralized allograft bone material.

18. A bone graft implant device of claim 17, wherein at least one of the amount of demineralization or area of the demineralized allograft bone material portion is adjustable to impart a desired flexibility to the implant body.

19. A bone graft implant device of claim 17, wherein the engagement member comprises at least one protrusion formed on opposing surfaces of the implant body.

20. A bone graft implant device of claim 1, wherein the implant device comprises 5% to about 50% by weight of demineralized bone based on a total weight of the implant device and the implant device comprises 95% to about 50% by weight of non-demineralized bone based on the total weight of the implant device.

* * * * *